US007030214B2

(12) United States Patent
Callens et al.

(10) Patent No.: US 7,030,214 B2
(45) Date of Patent: Apr. 18, 2006

(54) UREINS DERIVED FROM α, ω, DIAMINO ACIDS AND PROCESS FOR THEIR PREPARATION

(75) Inventors: Roland Callens, Drongen (BE); Georges Blondeel, Aalst (BE); Marc Anteunis, Mariakerke (BE); Frank Becu, Jabbeke (BE)

(73) Assignee: Solvay (Societe Anonyme), (BE)

( * ) Notice: Subject to any disclaimer, the term of this patent is extended or adjusted under 35 U.S.C. 154(b) by 675 days.

(21) Appl. No.: 09/944,209

(22) Filed: Sep. 4, 2001

(65) Prior Publication Data

US 2002/0058784 A1    May 16, 2002

Related U.S. Application Data

(60) Division of application No. 09/502,561, filed on Feb. 11, 2000, now Pat. No. 6,310,178, which is a continuation of application No. 08/985,658, filed on Jun. 17, 1997, now Pat. No. 6,060,586, which is a division of application No. 08/257,292, filed on Jun. 9, 1994, now abandoned.

(30) Foreign Application Priority Data

Jun. 18, 1993    (BE) .................................. 09300621

(51) Int. Cl.
    *A61K 38/05*    (2006.01)
(52) U.S. Cl. ..................... 530/331; 548/468; 562/557
(58) Field of Classification Search ................ 530/331; 548/468; 562/557
    See application file for complete search history.

(56) References Cited

U.S. PATENT DOCUMENTS

| | | | | |
|---|---|---|---|---|
| 2,288,422 | A | 6/1942 | Rohm | ................... 260/506 |
| 3,928,305 | A | 12/1975 | Werle | .................. 260/112.5 |
| 4,045,556 | A * | 8/1977 | Schwertner et al. | .......... 424/177 |
| 4,515,803 | A | 5/1985 | Henning et al. | ............. 514/338 |
| 4,980,384 | A | 12/1990 | Takahashi et al. | .......... 435/106 |
| 5,032,577 | A | 7/1991 | Fung et al. | .................... 514/18 |
| 5,198,533 | A | 3/1993 | Schally et al. | .............. 530/313 |
| 5,312,831 | A * | 5/1994 | Ayral-Kaloustian et al. | .......... 514/478 |

FOREIGN PATENT DOCUMENTS

| | | |
|---|---|---|
| AU | 86/59209 | 6/1986 |
| EP | 0074070 | 3/1983 |
| EP | 0207358 | 1/1987 |
| JP | 56-147757 | 11/1981 |

OTHER PUBLICATIONS

Wilchek, M. et al "Limitations of N-hydroxysuccinimide esters in affinity chromatography" Biochemistry, vol. 26, pp. 2155-2161, 1987.*
Tuomanen E. et al "Protection by D-amino acids against growth inhibition" Antimicrob. Agents Chemother., vol. 26, No. 3, pp. 414-416, 1984.*
Kessler, H. et al "Structural optimization of peptides for cytoprotection of rat liver cells" Pept. Chem. pp. 627-630, 1988.*
Caplus abstract 1988:522636, 1988.*
Kemp et al., Organic Chemistry, Worth Publishers, Inc. (1980).*
Lehninger, Principles of Biochemistry, Worth Publishers, Inc. (1982).*
J.T. Capecchi et al. "Critical Examination of a Method for the Analysis of α and _Linkages in Peptides Containing Aspartic Acid and Glutamic Acid". Journal of Organic Chemistry, vol. 48, No. 12, Jun. 17, 93, p. 2014-2021.
H. Maeda et al.: "Synthesis and central nervous system actions of thyrotropin-releasing hormone analogs containing a 1-substituted 2-oxoimadazolidine moiety". Int. Journal of Peptide and Protein Research, p. 403-411.
M. Suzuki et al.: "Synthesis and central nervous system actions of thyrotropin-releasing hormone analogues containing a dihydroorotic acid moiety". Journal of Medicinal Chemistry, vol. 33, No. 8, p. 2130-2137.
E. Müller: "Methoden der organischen Chemie". Houben-Weyl, 1974, vol. XV/1, p. 472.
March, Adv Org Chem 278-286.

* cited by examiner

*Primary Examiner*—Leigh C. Maier
(74) *Attorney, Agent, or Firm*—Connolly Bove Lodge & Hutz

(57) ABSTRACT

Ureins are obtained by reaction, in basic medium, between an $N^\omega$-(aryloxycarbonyl)diamino acid and a compound containing a free amino group. The chirality of the compounds is outstandingly well preserved.

15 Claims, No Drawings

UREINS DERIVED FROM α, ω, DIAMINO ACIDS AND PROCESS FOR THEIR PREPARATION

RELATED APPLICATIONS

This application is a divisional application of Ser. No. 09/502,561, filed Feb. 11, 2000, which is issued as U.S. Pat. No. 6,310,178, which is a continuation application of Ser. No. 08/985,658, filed on Jun. 17, 1997, which issued as U.S. Pat. No. 6,060,586, which is a divisional of Ser. No. 08/257,292, filed on Jun. 9, 1994 which is now abandoned which claims benefit to Belgium Application No. 09300621 filed Jun. 18, 1993.

The present invention relates to new ureins derived from α,ω-diamino acids and to a new process for the preparation of such compounds.

Ureins derived from diamino acids can conventionally be prepared by carbamoylation by means of a cyanate or of an isocyanate. This known procedure does not, however, appear entirely satisfactory, mainly due to insufficient specificity of these reactants for the amino functional group to be carbamoylated and due to the sometimes significant racemization which such a treatment can cause.

The invention overcomes the disadvantages of the conventional processes by providing a new, particularly outstanding, process which makes it possible to obtain the desired product with an improved chemical yield while retaining outstandingly well the chiral purity of the compounds used.

The invention consequently relates to a process for the preparation of ureins derived from an α,ω-diamino acid, according to which a compound containing a free amino group is reacted, in basic medium, with a diamino acid derivative containing an $N^{\omega}$-aryloxycarbonyl group.

Urein is understood to denote any compound whose molecular structure contains the structure —NH—CO—NH—.

Amino acid is understood to denote, for the purposes of the present invention, any compound comprising at least one amino group and at least one carboxyl group. By extension, the term "amino acid" is also understood to encompass hereinbelow any amino acid in which certain other groups are optionally bonded to organic groups such as protective groups. In particular, α,ω-diamino acid is understood to denote any amino acid comprising at least one amino group and at least one carboxyl group bonded to the same carbon atom of the molecule and additionally comprising at least one other amino group bonded to another carbon atom. It most often concerns a compound of general formula

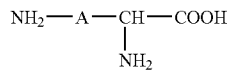

in which A represents a bivalent group consisting of a carbon chain containing 1 to 8 carbon atoms, which chain is optionally substituted by one or a number of groups chosen from $C_1$–$C_3$ alkyl groups and functional groups comprising at least one oxygen or sulphur atom such as a carboxyl, acyl, hydroxyl, alkoxy or mercapto group, without the total number of carbon atoms in the group A being greater than 15. A is preferably a polymethylene group comprising from 2 to 5 carbon atoms. Mention may be made, as examples of α,ω-diamino acids, of especially 2,3-diaminopropanoic acid, 2,4-diaminobutanoic acid, ornithine, lysine, homolysine, 5-hydroxylysine, 6-methyllysine and 2,6-diaminopimelic acid.

Diamino acid derivative containing an $N^{\omega}$-aryloxycarbonyl group, also subsequently known as $N^{\omega}$-(aryloxycarbonyl)diamino acid, is understood to denote any α,ω-diamino acid derivative in which an aryloxycarbonyl group of formula R—O—CO—, R symbolizing an aryl group, is bonded to the nitrogen atom of the ω-amino group of the diamino acid.

In the process according to the invention, the use of a diamino acid derivative containing an $N^{\omega}$-aryloxycarbonyl group is critical. In fact, it is apparent, surprisingly, that the aryloxycarbonyl group bonded to the ω-amino group of the amino acid leads, in the presence of a compound containing a free amino group, to the formation of a urein by substitution of the aryloxy fragment of the said aryloxycarbonyl group by the free amino group of the said compound.

The $N^{\omega}$-aryloxycarbonyl derivative of the diamino acid used generally contains, as aryloxycarbonyl group, a group comprising from 7 to 15 carbon atoms. This aryloxycarbonyl group is most often a phenyloxycarbonyl or naphthyloxycarbonyl group optionally substituted by at least one group chosen from alkyl groups comprising from 1 to 4 carbon atoms and the nitro group. Mention may be made, as examples of aryloxycarbonyl groups which can be used in the process according to the invention, of the phenyloxycarbonyl, tolyloxycarbonyl, xylyloxycarbonyl, mesitylyloxycarbonyl, ethylphenyloxycarbonyl, diethylphenyloxycarbonyl, propylphenyloxycarbonyl, isopropylphenyloxycarbonyl, naphthyloxycarbonyl and nitrophenyloxycarbonyl groups. The aryloxycarbonyl group is preferably a phenyloxycarbonyl or p-tolyloxycarbonyl group. Good results have been obtained in the process according to the invention with the $N^{\omega}$-phenyloxycarbonyl derivative of the diamino acid.

An $N^{\omega}$-aryloxycarbonyl derivative of any α,ω-diamino acid can be used in the process according to the invention.

The $N^{\omega}$-(aryloxycarbonyl)diamino acid is a product which is inexpensive and readily accessible. It can be prepared conventionally by resorting to well known selective acylation techniques, for example via the copper complex according to a procedure similar to that described in particular in "Methoden Der Organischen Chemie" (Houben-Weyl), 1974, Volume XV/1, p. 472, concerning $N^{\epsilon}$-benzyloxycarbonyl-L-lysine. As the α-amino functional group is complexed by the copper ion, the aryloxycarbonyl group can be selectively attached to the ω-amino functional group of the diamino acid by reaction with an aryl chloroformate or an aryloxycarbonyloxysuccinimide.

The compound comprising a free amino group which reacts with the $N^{\omega}$-(aryloxycarbonyl)diamino acid in the process according to the invention is any compound of general formula R1R2NH in which R1 and R2 represent, independently of one another, hydrogen atoms or alkyl, cycloalkyl or aralkyl radicals or in which R1 and R2 together form an alicyclic radical. In this compound, the alkyl, cycloalkyl, aralkyl or alicyclic radicals can be substituted by one or a number of functional groups comprising at least one oxygen, sulphur or nitrogen atom, for example by a carboxyl, hydroxyl, mercapto, indolyl or imidazolyl group. Compounds which can be used in the process according to the invention are in particular ammonia, primary or secondary amines and the amino acids as defined above. The process according to the invention is particularly advantageous when the compound comprising a free amino group is an amino acid.

When the N$^ω$-(aryloxycarbonyl)diamino acid is a derivative of an α,ω-diamino acid in which the carbon chain of the group A consists of 1 to 3 carbon atoms, the N$^ω$-(aryloxycarbonyl)diamino acid acts, in the process according to the invention, both as N$^ω$-aryloxycarbonyl derivative and, via its α-amino group, as compound containing a free amino group. The result thereof, via an intramolecular reaction, is the formation of cyclic ureins of general formula

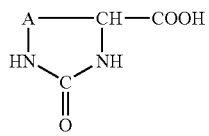

in which A represents a bivalent group consisting of an optionally substituted linear carbon chain formed from 1 to 3 carbon atoms.

In the process of the invention, by way of illustration, N$^β$-aryloxycarbonyl-2,3-diaminopropanoic acid forms 2-oxoimidazolidinyl-4-carboxylic acid, N$^γ$-aryloxycarbonyl-2,4-diaminobutyric acid forms 2-oxohexahydropyrimidinyl-4-carboxylic acid and N$^δ$-(aryloxycarbonyl)ornithine forms 2-oxohexahydro-1,3-diazepinyl-4-carboxylic acid.

When the N$^ω$-(aryloxycarbonyl)diamino acid is a derivative of an α,ω-diamino acid in which the carbon chain of the group A consists of at least 4 carbon atoms, the N$^ω$-(aryloxycarbonyl)diamino acid is converted, in the process according to the invention, into a non-cyclic urein of general formula

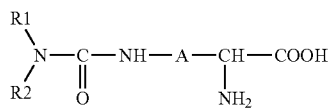

in which R1 and R2 have the same meaning as above and in which A represents a bivalent group consisting of an optionally substituted linear carbon chain formed from at least 4 carbon atoms. In the process of the invention, by way of illustration, homocitrulline is obtained by reaction between N$^ε$-(phenyloxycarbonyl)lysine and ammonia. When the compound comprising a free amino group is an amino acid, an N$^ω$-(carboxyalkylcarbamoyl)-α,ω-diamino acid is obtained by the process according to the invention.

An N$^ω$-(aryloxycarbonyl)diamino acid incorporated in a peptide chain can, without disadvantage, be used in the process according to the invention. In particular, when the N$^ω$-(aryloxycarbonyl)diamino acid is a derivative of an α,ω-diamino acid in which the carbon chain of the group A consists of 1 to 3 carbon atoms and when this compound constitutes the N-terminal residue of a peptide chain, the process according to the invention makes it possible easily to obtain peptides of general formula

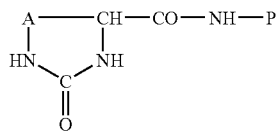

in which A represents a bivalent group consisting of an optionally substituted linear carbon chain formed from 1 to 3 carbon atoms and in which NH-P represents any peptide chain bonded to the cyclic urein via an amide bond.

The process according to the invention is carried out in a basic medium.

The process according to the invention is generally carried out in a liquid medium in which the N$^ω$-(aryloxycarbonyl)diamino acid and the compound comprising a free amino group are at least partially soluble and preferably entirely soluble. Depending on the nature of the reactants, the medium can comprise water and/or an organic solvent. Organic solvents which are suitable in the process according to the invention are lower alcohols such as in particular methanol, ethanol and isopropanol, tetrahydrofuran and dimethoxyethane. Media consisting of water and of a water-miscible organic solvent are preferred. Good results have been obtained in particular in a water/ethanol medium.

The basicity of the medium can be obtained by addition of a basic compound to the medium, for example by addition of an inorganic base such as LiOH, NaOH or KOH or by addition of an organic base which is inert under the reaction conditions, such as a tertiary amine. Good results have, in particular, been obtained in the presence of LiOH or of triethylamine. When the compound containing a free amino group is an amino acid containing free carboxyl functional groups, the basic compound must be used in an amount sufficient to neutralize the carboxyl functional groups.

In order to obtain cyclic ureins, the intra-molecular reactivity of the N$^ω$-(aryloxycarbonyl)diamino acid is such that it is possible, without problems, to add a compound containing a free amino group, such as ammonia, to achieve the desired basicity of the medium, without this appreciably affecting the yield of the reaction in cyclic urein.

In order to obtain non-cyclic ureins, when the α-amino group of the N$^ω$-(aryloxycarbonyl)diamino acid is free, it is necessary, in order to avoid a condensation reaction of the N$^ω$-(aryloxycarbonyl)diamino acid concurrent with the desired reaction with the compound containing a free amino group, to operate with an excess, with respect to the stoichiometric amount necessary, of the compound containing a free amino group which it is desired to react with the N$^ω$-(aryloxycarbonyl)diamino acid. Good results are obtained when the reaction is carried out with a molar ratio of the compound containing a free amino group to the N$^ω$-(aryloxycarbonyl)diamino acid which is at least equal to 3. The reaction is preferably carried out with a ratio at least equal to 4. In principle, there is no upper limit to this ratio. In practice, however, it is generally pointless to carry out the reaction with a molar ratio of the compound containing a free amino group to the N$^ω$-(aryloxycarbonyl)diamino acid which is greater than 100. The molar ratio most often does not exceed 10. When the compound containing a free amino group is an amino acid or a peptide, the molar ratio preferably does not exceed 7. When the compound containing a free amino group has a sufficiently basic nature, it may prove to be pointless to add another basic compound to the medium.

The process according to the invention can be implemented in a wide concentration range of the reactants in the liquid medium, in particular for obtaining cyclic ureins. The N$^ω$-(aryloxycarbonyl)diamino acid is generally used at a concentration of 0.05 to 5 mol/l, preferably of 0.1 to 1 mol/l.

The reaction can be carried out from room temperature to the boiling temperature of the organic solvent. It is advantageously carried out from 30 to 80° C. A temperature of 40 to 60° C. as very particularly preferred.

Under these conditions, the reaction time is generally less than 10 hours. The reaction is most often complete after a time of 30 minutes to 4 hours.

The process according to the invention appears particularly advantageous for preparing ureins derived from α,ω-diamino acids. The N^ω-aryloxycarbonyl derivative for the diamino acid used in the process according to the invention can be easily and cheaply prepared from the diamino acid. It can easily be isolated in the pure form. It is stable and can be stored for a long time without deteriorating. The process according to the invention is particularly outstanding. It makes it possible to obtain the desired ureins with a very high yield. It additionally has very little effect on the chirality of the compounds used. Moreover, the departure of the aryloxy fragment of the aryloxycarbonyl group only generates relatively inoffensive by-products in the medium which do not disturb the synthesis. For example, when it concerns the phenyloxycarbonyl group, only phenol is generated. Consequently, when the compounds used contain very labile groups, such as certain protective groups, the by-products generated in the medium do not cause any damage to these compounds. Purification of the desired products is markedly simpler than in the previous known processes.

The invention also relates to N^ω-carboxyalkylcarbamoyl-α,ω-diamino acids, ureins derived from an α,ω-diamino acid, of general formula

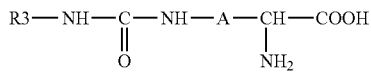

in which A represents a bivalent group consisting of a linear carbon chain formed from 4 to 8 carbon atoms, which chain is optionally substituted by one or a number of groups chosen from $C_1$–$C_3$ alkyl groups and functional groups comprising at least one oxygen or sulphur atom such as a carboxyl, acyl, hydroxyl, alkoxy or mercapto group, and in which R3—NH represents an amino acid or a peptide. A is preferably a polymethylene group containing 4 or 5 carbon atoms. R3—NH is preferably an amino acid and more preferentially an essential amino acid.

These new compounds constitute compounds with a structure similar to that of dipeptides and can be used in particular in place of the corresponding dipeptides, in particular as a source of essential amino acids in parenteral human feeding or in animal feeding.

The invention also relates to the cyclic ureins of general formula

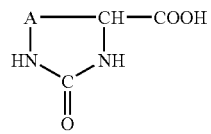

in which A represents a bivalent group consisting of a linear carbon chain formed from 1 to 3 carbon atoms, which chain is optionally substituted by one or a number of groups chosen from $C_1$–$C_3$ alkyl groups and functional groups comprising at least one oxygen or sulphur atom such as a carboxyl, acyl, hydroxyl, alkoxy or mercapto group, with the exception of 2-oxoimidazolidinyl-4-carboxylic acid and (LD)-2-oxohexahydropyrimidinyl-4-carboxylic acid. A preferably represents a bivalent group consisting of an optionally substituted carbon chain consisting of 2 or 3 carbon atoms. In a particularly preferred way, A represents a trimethylene group —$(CH_2)_3$—. In this case, the urein formed is 2-oxohexahydro-1,3-diazepinyl-4-carboxylic acid, easily obtained by the process according to the invention from ornithine.

Depending on whether the (D) or (L) enantiomer of the diamino acid is used in the process according to the invention, the (D) or (L) enantiomer of the corresponding cyclic urein is obtained in the chirally pure form.

These cyclic ureins can be used in particular as the N-terminal residue of certain biologically active peptides, such as the hormone TRH (Thyrotropin Releasing Hormone), by replacing the N-terminal pyroglutamyl group of this peptide.

Finally, the invention relates to peptides analogous to TRH, of general formula

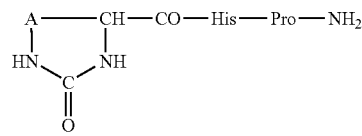

in which A is a bivalent group consisting of a linear carbon chain formed from 2 or 3 carbon atoms, which chain is optionally substituted by one or a number of groups chosen from $C_1$–$C_3$ alkyl groups and functional groups comprising at least one oxygen or sulphur atom such as a carboxyl, acyl, hydroxyl, alkoxy or mercapto group. A is preferably a polymethylene group. The peptide in which A is a trimethylene group is preferred. These peptides have an increased resistance to proteolytic digestion while retaining a high biological activity.

The symbolic representations of the amino acids and of the peptides adopted in the description and examples follow the IUPAC nomenclature recommendations generally adopted and described, for example, in "Nomenclature and Symbolism for Amino Acids and Peptides, Recommendations 1983", Eur. J. Biochem. (1984), 138, p. 9–37. Except when otherwise stipulated, all the amino acids described are (L)-amino acids.

The following examples illustrate the invention.

The various products and synthetic intermediates reported in the examples were characterized by various analytical methods used under the following conditions:

optical rotation (α): measured at 589 nm at 25° C.

Thin layer chromatography (TLC):
  Merck 60F-254 silica gel plates
  eluents:
    $R_f(1)$ Ethyl acetate:n-butanol:acetic acid:water 1:1:1:1
    $R_f(2)$ Acetonitrile:chloroform:acetic acid:water 5:2:2:1
    $R_f(3)$ Acetonitrile:chloroform:acetic acid:water 7:4:4:2

HPLC chromatography:
  5 μm Vydac C-18 column
  Elution: 98% A+2% B to 25% A+75% B gradient over 49 minutes (A=water containing 0.1% trifluoroacetic acid; B=acetonitrile containing 0.1% trifluoroacetic acid)
  Flow rate=2 ml/min Detection: 220 nm UV
Nuclear magnetic resonance (NMR):
500 MHz Brüker AMX apparatus
Shift given in ppm
Appearances of the resonances:
  m=multiplet,
  s=singlet,
  d=doublet,
  t=triplet,
  q=quartet,
  quint=guintet,
  o=octet.

EXAMPLE 1

Synthesis of $N^\epsilon$-($N^\alpha$-tryptophanocarbonyl)lysine 5.1 g (25 mmol) of tryptophan, 1.34 g (5 mmol) of $N^\epsilon$-(phenyloxycarbonyl)lysine and 1.05 g (25 mmol) of $LiOH \cdot H_2O$ were weighed into a 100 ml round-bottomed flask and then 40 ml of water were introduced into the round-bottomed flask. The latter was immersed in an oil bath maintained at 75° C. for 45 minutes, was then rapidly cooled to room temperature under flowing water and then treated with 25 ml of hydrochloric acid. The precipitate formed was filtered, after leaving overnight in a refrigerator.

HPLC analysis showed complete conversion of the $N^\epsilon$-(phenyloxycarbonyl)lysine to 2 products having, under the analysis conditions, a retention time ($t_R$) of 12.23 and 13.95 minutes, with a 13:1 ratio in the peak surface areas. The products were separated by injecting the filtrate as is into a preparative C-18 HPLC column and then lyophilized. 880 mg of $N^\epsilon$-($N^\alpha$-tryptophanocarbonyl)lysine and 76 mg of $N^\epsilon$-($N^\alpha$-tryptophanocarbonyl)-$N^\alpha$-lysinocarbonyl) lysine were obtained.

The physicochemical properties of $N^\epsilon$-($N^\alpha$-tryptophanocarbonyl)lysine are the following:
M.p.: 133° C. α: +3.31 (c=1, 1% acetic acid) TLC: $R_f(3)$=0.34 NMR (H-1) in $d_6$-DMSO:

| | |
|---|---|
| 11.00 (1H, s), indole NH | 7.50 (1H, d), indole H4 |
| 7.32 (1H, d), indole H7 | 7.09 (1H, s), indole H2 |
| 7.03 (1H, t), indole HE | 6.94 (1H, t), indole H5 |
| 6.28 (1H, broad t), Lys εNH | 6.18 (1H, d), Trp αNH |
| 4.36 (1H, m), Trp Hα | 3.30 (1H, m), Lye Hα |
| 3.12 (1H, dd), Trp HβA | 2.99 (1H, dd), Trp HβB |
| 2.94 (2H, m), Lys Hε's | 1.70 (1H, m), Lys HβA |
| 1.60 (1H, m), Lys HβB | 1.31 (4H, m), Lys Hγ's + Hδ's |

EXAMPLE 2

Synthesis of $N^\epsilon$-(methioninocarbonyl)lysine $N^\epsilon$-(Methioninocarbonyl)lysine was prepared from methionine and $N^\epsilon$-(phenyloxycarbonyl)lysine according to the same recipe as that described in Example 1. It has the following physicochemical properties:
M.p.: 148° C. α: −9.5 (c=1, 1% acetic acid) TLC: $R_f(3)$=0.27 HPLC: $t_R$=7.14 min NMR (H-1) in $d_6$-DMSO:

| | |
|---|---|
| 6.43 (1H, broad d), Met NHα | 6.33 (1H, broad t), Lys NHε |
| 4.11 (1H, m), Met Hα | 3.35 (1H, m), Lys Hα |

-continued

| | |
|---|---|
| 2.95 (2H, m), Lys Hε's | 2.33 (2H, t), Met Hγ's |
| 2.02 (3H, s), Met $CH_3$ | 1.88 (1H, m), Met HβA |
| 1.77 (1H, m), Met HβB | 1.72 (1H, m), Lys HβA |
| 1.65 (1H, m), Lys HβB | 1.33 (4H, m), Lys Hγ's + Hδ's |

EXAMPLE 3

Synthesis of (D)-2-oxohexahydro-1,3-diazepinyl-4-carboxylic acid 7.7 ml (±100 mmol) of 25% aqueous ammonia were added to a suspension of 1.27 g (5 mmol) of (D)-$N^\delta$-(phenyloxycarbonyl)ornithine in 15 ml of dimethoxyethane and 10 ml of water. The degree of conversion was monitored by TLC. Once the (D)-(phenyloxycarbonyl)ornithine had disappeared, the reaction mixture was concentrated to dryness. The residue was triturated with 20 ml of 80% acetone, filtered and dried. At this stage, it was determined by NMR that the crude product obtained was the ammonium salt of (D)-2-oxohexahydro-1,3-diazepinyl-4-carboxylic acid, contaminated with approximately 5% of citrulline (Yield: 820 mg or 92% as crude product). (D)-2-Oxohexahydro-1,3-diazepinyl-4-carboxylic acid was obtained, with a purity greater than 98%, by passing the crude product as an aqueous solution through an ion exchange resin column in the $H^+$ form and then lyophilizing.

M.p.: 130–150° C. (decomposition) α: +14.6 (c=1, water) TLC: $R_f(3)$: 0.70 no longer reacting with ninhydrin $R_f(3)$: 0.16 for citrulline $R_f(3)$: 0.54 for $N^\delta$-(phenyloxycarbonyl)ornithine NMR(H), ref $d_6$-DMSO at 2.49:

| | |
|---|---|
| 6.20 (1H, broad s), NH1 | 5.5 (1H, broad s), NH3 |
| 3.75 (1H, m) H4 | 2.89 (2H, m) H7 |
| 1.90 (1H, m) H5A | 1.77 (1H, m) H5B |
| 1.55 (2H, m), 6 H's | |

NMR(C-13) ref $d_6$-DMSO at 39.50:

| | |
|---|---|
| 173.45 (COOH) | 163.65 (C2) |
| 54.43 (C4) | 31.03 (C5) |
| 26.81 (C6) | |

EXAMPLE 4

Synthesis of (L)-2-oxohexahydropyrimidinyl-4-carboxylic acid 2 g (8.3 mmol) of (L)-$N^\gamma$-(phenyloxycarbonyl)diaminobutyric acid were dissolved in 10 ml of water and 5 ml of methanol. After addition of 3 ml (22 mmol) of triethylamine, the solution was heated under gentle reflux until the starting material had completely disappeared (monitoring by TLC). The solution was concentrated to dryness and then suspended in 50 ml of dichloromethane. The product, then in the triethylamine (L)-2-oxohexahydropyrimidinyl-4-carboxylate form, was displaced by addition of 1.8 ml of trifluoroacetic acid. As triethylamine trifluoroacetate is very soluble, (L)-2-oxohexahydropyrimidinyl-4-carboxylic acid selectively precipitates. It was recovered by filtration, washed with dichloromethane and then dried.

Yield: 95% α: +20.1 (c=1, water) TLC: $R_f(2)$=0.55 NMR ($^1$H) ref D$_2$O at 4.80:

| | |
|---|---|
| 4.27 (1H, t), Hα | 3.35 (1H, d of t), HγA |
| 3.22 (1H, o), HγB | 2.13 to 2.18 (2H, m), HβA + B |

EXAMPLE 5

Synthesis of (2-oxohexahydro-1,3-diazepinyl-4-carbonyl)-His-Pro-NH$_2$ 1 g (1.40 mmol) of Nδ-(phenyloxycarbonyl)Orn-His-Pro-NE$_2$ bis(trifluoroacetate) was dissolved in 10 ml of methanol containing 0.75 ml (5.4 mmol) of triethylamine. The solution was brought to gentle reflux at a temperature of approximately 65° C. until the starting material had disappeared (monitoring by TLC). The solution was concentrated to dryness and triturated with 20 ml of dichloromethane. After filtration, the crude product collected (0.52 g) was purified by C-4 reverse phase preparative chromatography. The analytical sample isolated in the acetate salt form has the following physicochemical properties;

α=−8.1 (c=1, 1% acetic acid) M.p.: 105° C. TLC $R_f(1)$=0.42 NMR ($^1$H, D$_2$O): Some resonances are split due to the cis/trans isomerism at the His-Pro bond. The results for the major form (±85%) are taken up below:

| | |
|---|---|
| 8.56 (1H, s), imidazole H2 | 7.34 (1H, s), imidazole H5 |
| 5.08 (1H, dd), His Hα | 4.46 (1H, dd), Pro Hα |
| 4.07 (1H, dd), Odc Hα | 3.81 (1H, m), Pro HδA |
| 3.65 (1H, m), Pro HδB | 3.30 (1H, d), His HβA |
| 3.19 (1H, dd), His HβB | 3.08 to 3.02 (2H, m), Odc HδA + B |
| 2.36 (1H, m), Pro HβA | 2.15 to 1.95 (5H + acetate CH$_3$) |
| 1.74 (1H, m) Odc HγA | 1.51 (1H, m), Odc HγB |

EXAMPLE 6

Synthesis of (2-oxohexahydropyrimidinyl-4-carbonyl)His-Pro-NH$_2$ 432 mg (3 mmol) of (L)-2-oxohexahydropyrimidine-4-carboxylic acid were dissolved in 10 ml of N-methylpyrrolidone containing 0.33 ml (3 mmol) of N-methylmorpholine. 0.39 ml of isobutyl chloroformate were added to the solution cooled to −10° C. After reacting for 5 minutes at −10° C., a solution of 5 ml of N-methylpyrrolidone containing 1.25 g (3 mmol) of His-Pro-NH$_2$.2HBr and 0.90 ml of triethylamine (6.5 mmol) was added. After maturing for a time of 30 minutes at room temperature, the reaction mixture was added dropwise to 50 ml of ethyl ether. The precipitate obtained was filtered, then washed twice with 20 ml of dichloromethane and dried, giving 1.3 g of product. It was purified by passing through a column of silica gel, the same mobile phase being used as in TLC.

Analytical data: α=−23.8 (c=1, acetic acid) M.p.=140° C. TLC: $R_f(1)$=0.33 NMR($^1$H) in D$_2$O. Some resonances are split due to the cis/trans isomerism at the His-Pro bond. The results for the major form (±85%) are taken up below:

| | |
|---|---|
| 8.16 (1H, s), imidazole H2 | 7.21 (1H, s), imidazole H5 |
| 5.04 (1H, dd), His Hα | 4.48 (1H, dd), Pro Hα |
| 4.17 (1H, broad s), Opc Hα | 3.88 (1H, m), Pro HδA |
| 3.68 (1H, m), Pro HδB | 3.30 (2H, broad d), His HβA + Opc HγA |
| 3.14 (1H, dd), His HβB | 2.78 (1H, m), Opc HγB |
| 2.37 (1H, m) Pro HβA | 2.20 to 2.00, Pro HβB + Hγ's/Opc Hβ's |

What is claimed is:

1. N$^\omega$-Carboxyalkylcarbamoyl-α,ω-diamino acids of general formula

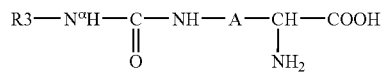

in which A represents a bivalent group consisting of a linear carbon chain formed from 4 to 8 carbon atoms, which chain is optionally substituted by one or a number of groups chosen from C$_1$–C$_3$ alkyl groups and functional groups comprising at least one oxygen or sulphur atom and in which R3-N$^\alpha$H represents an α-amino acid or a peptide comprising the α-amino acid and the N$^\alpha$ is a nitrogen atom attached to the α-carbon of the α-amino acid.

2. N$^\omega$-Carboxyalkylcarbamoyl-α,ω-diamino acid as claimed in claim 1, wherein R3-N$^\alpha$H— is an α-amino acid.

3. N$^\omega$-Carboxyalkylcarbamoyl-α,ω-diamino acid as claimed in claim 1, wherein R3-N$^\alpha$H— is an essential α-amino acid.

4. N$^\omega$-Carboxyalkylcarbamoyl-α,ω-diamino acid as claimed in claim 1, wherein R3-N$^\alpha$H— is tryptophane.

5. N$^\omega$-Carboxyalkylcarbamoyl-α,ω-diamino acid as claimed in claim 1, wherein R3-N$^\alpha$H— is methionine.

6. N$^\omega$-Carboxyalkylcarbamoyl-α,ω-diamino acid as claimed in claim 1, wherein the linear carbon chain is substituted by a functional group comprising at least one oxygen atom.

7. N$^\omega$-Carboxyalkylcarbamoyl-α,ω-diamino acid as claimed in claim 6, wherein, the functional group comprising at least one oxygen atom is selected from carboxyl, acyl, hydroxyl and alkoxy group.

8. N$^\omega$-Carboxyalkylcarbamoyl-α,ω-diamino acid as claimed in claim 1, wherein the linear carbon chain is substituted with a functional group containing sulphur.

9. N$^\omega$-Carboxyalkylcarbamoyl-α,ω-diamino acid as claimed in claim 8, wherein the functional group containing sulphur is a mercapto group.

10. N$^\omega$-Carboxyalkylcarbamoyl-α,ω-diamino acid as claimed in claim 1, wherein the linear carbon chain is a polymethylene group.

11. N$^\omega$-Carboxyalkylcarbamoyl-α,ω-diamino acid as claimed in claim 1, wherein said functional group is selected from the group consisting of carboxyl, hydroxyl, alkoxy and mercapto group.

12. A peptide of general formula

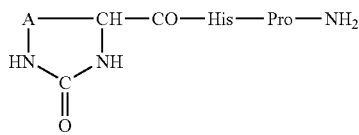

in which A is a bivalent group consisting of a linear carbon chain formed from 2 carbon atoms, which chain is substituted by at least one substituent selected from the group consisting of a functional group comprising at least one sulphur atom and a functional group comprising at least one oxygen atom selected from carboxyl, acyl, hydroxyl and alkoxy group.

13. The peptide according to claim 12, in which the linear carbon chain is substituted with a functional group containing sulphur.

14. The peptide according to claim 13, in which the functional group containing sulphur is a mercapto group.

15. The peptide according to claim 12, wherein said functional group is selected from the group consisting of carboxyl, hydroxyl, alkoxy and mercapto group.

* * * * *

UNITED STATES PATENT AND TRADEMARK OFFICE
CERTIFICATE OF CORRECTION

PATENT NO. : 7,030,214 B2  Page 1 of 1
APPLICATION NO. : 09/944209
DATED : April 18, 2006
INVENTOR(S) : Roland Callens et al.

It is certified that error appears in the above-identified patent and that said Letters Patent is hereby corrected as shown below:

On the Front Page:

The Title, Item (54) "UREINS DERIVED FROM α, ω, DIAMINO ACIDS AND PROCESS FOR THEIR PREPARATION" should read -- UREINS DERIVED FROM α, ω-DIAMINO ACIDS AND PROCESS FOR THEIR PREPARATION --

In the Claims:

In Claim 1, at column 10, lines 30-31 "R3-$N^{\alpha}$H represents an α-amino acid or a peptide comprising the α-amino acid and the $N^{\alpha}$ is a nitrogen atom attached to" should read --R3-$N^{\alpha}$H represents an α-amino acid and $N^{\alpha}$ is a nitrogen atom attached to --

Signed and Sealed this

Twenty-sixth Day of September, 2006

JON W. DUDAS
*Director of the United States Patent and Trademark Office*